US010195441B2

(12) United States Patent
Kaiser et al.

(10) Patent No.: US 10,195,441 B2
(45) Date of Patent: *Feb. 5, 2019

(54) APPARATUS AND METHODS FOR OPTIMIZING INTRA-CARDIAC FILLING PRESSURES THROUGH CONTROLLED REGURGITATION

(71) Applicant: CardioFlow Technologies, LLC, Nashville, TN (US)

(72) Inventors: Daniel Walter Kaiser, Palo Alto, CA (US); Clayton A. Kaiser, Nashville, TN (US)

(73) Assignee: CARDIOFLOW TECHNOLOGIES, LLC, Nashville, TN (US)

( * ) Notice: Subject to any disclaimer, the term of this patent is extended or adjusted under 35 U.S.C. 154(b) by 55 days.

This patent is subject to a terminal disclaimer.

(21) Appl. No.: 15/168,204

(22) Filed: May 30, 2016

(65) Prior Publication Data

US 2016/0346448 A1 Dec. 1, 2016

Related U.S. Application Data

(60) Provisional application No. 62/168,784, filed on May 30, 2015.

(51) Int. Cl.
*A61N 1/362* (2006.01)
*A61N 1/365* (2006.01)
(Continued)

(52) U.S. Cl.
CPC ........ *A61N 1/36571* (2013.01); *A61B 5/0215* (2013.01); *A61B 5/042* (2013.01);
(Continued)

(58) Field of Classification Search
CPC . A61B 5/02028; A61B 5/0215; A61B 5/0245; A61B 5/029; A61M 1/125; A61N 1/362
See application file for complete search history.

(56) References Cited

U.S. PATENT DOCUMENTS

| 4,467,807 A | 8/1984 | Bornzin |
| 4,535,774 A | 8/1985 | Olson |

(Continued)

OTHER PUBLICATIONS

Korean Intellectual Property Office, International Search Report for corresponding International Application No. PCT/US2016/034920, Applicant: Cardioflow Technologies, LLC, Form PCT/ISA/210, dated Sep. 19, 2016, 4 pages.

(Continued)

*Primary Examiner* — Allen Porter, Jr.
(74) *Attorney, Agent, or Firm* — William A. English; Vista IP Law Group LLP (57) ABSTRACT

Systems and methods are provided for optimizing hemodynamics within a patient's heart, e.g., to improve the patient's exercise capacity. In one embodiment, a system is configured to be implanted in a patient's body to monitor and/or treat the patient that includes at least one sensor configured to provide sensor data that corresponds to a blood pressure within or near the patient's heart; at least one adjustable component designed to cause blood to flow in a direction opposite to the normal direction (regurgitation) within the patient's heart; and a controller configured for adjusting the function of the at least one adjustable component based at least in part on sensor data from the at least one sensor.

20 Claims, 6 Drawing Sheets

(51) Int. Cl.
    *A61N 1/39*      (2006.01)
    *A61N 1/372*      (2006.01)
    *A61B 5/0215*      (2006.01)
    *A61B 5/042*      (2006.01)
    *A61B 5/145*      (2006.01)
    *A61B 5/1459*      (2006.01)
    *A61B 17/00*      (2006.01)
    *A61M 1/12*      (2006.01)

(52) U.S. Cl.
CPC ........ *A61B 5/1459* (2013.01); *A61B 5/14542* (2013.01); *A61N 1/3655* (2013.01); *A61N 1/36521* (2013.01); *A61N 1/36528* (2013.01); *A61N 1/36542* (2013.01); *A61N 1/36557* (2013.01); *A61N 1/36564* (2013.01); *A61N 1/36585* (2013.01); *A61N 1/37252* (2013.01); *A61N 1/3987* (2013.01); *A61B 2017/00026* (2013.01); *A61B 2017/00243* (2013.01); *A61B 2017/00575* (2013.01); *A61B 2017/00597* (2013.01); *A61M 1/12* (2013.01); *A61M 2230/005* (2013.01); *A61M 2230/20* (2013.01); *A61M 2230/30* (2013.01); *A61M 2230/42* (2013.01); *A61M 2230/63* (2013.01)

(56) References Cited

U.S. PATENT DOCUMENTS

| | | |
|---|---|---|
| 5,447,524 A | 9/1995 | Alt |
| 5,509,428 A | 4/1996 | Dunlop |
| 5,676,162 A | 10/1997 | Larson |
| 8,043,360 B2 | 10/2011 | McNamara et al. |
| 8,406,879 B2 | 3/2013 | Shuros et al. |
| 2002/0072680 A1 | 6/2002 | Schock |
| 2004/0034272 A1 | 2/2004 | Diaz |
| 2004/0111006 A1 | 6/2004 | Alferness et al. |
| 2004/0254483 A1 | 12/2004 | Zdeblick |
| 2005/0049692 A1 | 3/2005 | Numamoto et al. |
| 2006/0064059 A1 | 3/2006 | Gelfand et al. |
| 2006/0206029 A1 | 9/2006 | Yair |
| 2008/0195167 A1 | 8/2008 | Ryan |
| 2009/0137968 A1 | 5/2009 | Rottenberg |
| 2010/0056999 A1 | 3/2010 | Herrera Cedeno |
| 2010/0057192 A1 | 3/2010 | Celermajer |
| 2010/0222635 A1 | 9/2010 | Poirier |
| 2011/0190874 A1 | 8/2011 | Celermajer |
| 2012/0165928 A1 | 6/2012 | Nitzan |
| 2015/0094802 A1* | 4/2015 | Buchbinder .......... A61F 2/2454 623/2.18 |
| 2016/0030743 A1 | 2/2016 | Kaiser |
| 2016/0045312 A1* | 2/2016 | Braido ................. A61B 5/6862 623/2.37 |
| 2016/0199554 A1 | 7/2016 | Kaiser et al. |

OTHER PUBLICATIONS

Korean Intellectual Property Office, Written Opinion for corresponding International Application No. PCT/US2016/034920, Applicant: Cardioflow Technologies, LLC, Form PCT/ISA/237, dated Sep. 19, 2016, 7 pages.

* cited by examiner

APPARATUS AND METHODS FOR OPTIMIZING INTRA-CARDIAC FILLING PRESSURES THROUGH CONTROLLED REGURGITATION

RELATED APPLICATION DATA

The present application claims benefit of provisional application Ser. No. 62/168,784, filed May 30, 2015, and is related to co-pending application Ser. No. 14/597,190, filed Jan. 14, 2015, which claims benefit of provisional application Ser. No. 61/927,038, filed Jan. 14, 2014, the entire disclosures of which are expressly incorporated by reference herein.

FIELD OF THE INVENTION

The present invention relates to apparatus, systems, and methods to optimize hemodynamics within a patient's heart, e.g., in order to improve exercise capacity.

BACKGROUND

In healthy young individuals, increasing left-sided filling pressures within the individual's heart is associated with a proportional increase in left ventricular stroke volume; and therefore cardiac output. However, with age, the left ventricle becomes more stiff over time. This process, often accelerated with decades of hypertension or diabetes, results in a failure of increased pressure to increase stroke volume. This pressure-volume relationship is also known as the Frank-Starling curve. Over time, the slope of this curve becomes flat. When this occurs, increasing left-sided filling pressures do not (or do so marginally) improve stroke volume. In some cases, high left-sided filling pressures result in mistral regurgitation and a reduction in cardiac output. As a result, the normal feedback mechanism of increasing blood flow to the heart the body attempts to increase cardiac output (such as during periods of exercise), no longer improves forward flow. Instead, the increased blood flow to the left ventricle results in rising left-sided filling pressures.

Computer modeling has revealed that differences in big-ventricular function are likely more important than total cardiac output in terms of patient symptoms. However discordant the ventricular function may be, the cardiac output of each ventricle must be the same. Therefore, with predominant left heart failure, pressure builds behind the left ventricle. In predominant right heart failure, pressure builds behind the right ventricle. Of importance, exercise/exertion exaggerates differences in ventricular function. Over time and accelerated by disease, most left ventricles develop some degree of diastolic dysfunction. Accordingly, during exercise, the left ventricle cannot "keep up with" the right ventricle. The resulting equilibrium results in rapid elevations in left-sided filling pressures during exercise that limit exercise capacity. An interactive device that can limit the rise in intra-cardiac filling pressures while maintaining cardiac output would dramatically improve exercise capacity and improve patient symptoms of fatigue and shortness of breath.

Long standing elevated left trial (LA) pressure can dilate the left atrium and contribute to trial arrhythmias such as atrial fibrillation. It is likely that increases in ventricular pressures (both right and left ventricular pressures) may result in ventricular arrhythmias as well. By maintaining lower intra-cardiac filling pressures, a system that maintains cardiac output while preventing elevated intra-cardiac pressures may decrease deadly cardiac arrhythmias.

Cardiac output and heart rate have a complicated relationship. Typically, in patients without volume overload, increasing heart rate does not affect cardiac output. This apparent paradox occurs due to a decrease in ventricular filling time and a redistribution of blood from the heart to peripheral tissue. When venous return to the heart is not increased, the stroke volume will fall with increasing heart rate implying an extrathoracic venous collapse. However, in patients that have a more flat pressure-volume relationship, increasing the heart rate can maintain stroke volume and increase cardiac output significantly. The amount of improvement in cardiac output typically depends on the ability of the left ventricle to relax fast enough at higher heart rates. Therefore, optimizing cardiac output is a complex interaction between volume status, heart rate, bi-ventricular pressure-volume curves, and filling parameters.

While increasing cardiac output, increasing heart rate may also increase left-sided filling pressures and exacerbate shortness of breath. Left-sided filling pressures may rise significantly with only marginal improvement in cardiac output. Therefore, the relationships between cardiac output and heart rate in response to changes in left-sided filling pressures and/or changes in heart rate are an important consideration to optimize filling pressures and cardiac output.

Increasing left-sided filling pressures may result in hyperventilation and may contribute to relative bradycardia. Both mechanisms may limit exercise capacity. Animal cork from the 1950's to the early 2000's have identified various receptors that are intimately intertwined with the autonomic nervous system and respiratory function. Increased left-sided filling pressures activate:

1. rapidly adapting receptors (RAR), [Coleridge and Coleridge, 1977b]
2. pulmonary receptors [Ravi and Kappagoda, 1992]
3. bronchial C-fiber receptors [Gunawardena et al., 2002]
4. Slowly adapting stretch receptors [Marshall and Widdicombe, 1958].

Therefore, all four types of pulmonary vagal sensory receptors are activated with elevated left-side side filling pressures, which result in increased respiratory rate.

Preventing increased left-sided filling pressures will therefore improve respiratory rate; and therefore improve exercise capacity in any individual with rising left-sided filling pressures with exercise. Recent human studies have found that even "healthy" individuals, without a diagnosis of heart failure, frequently develop moderate increases in left-sided filling pressures with mild exercise. This device has the potential to improve exercise capacity in these subjects.

SUMMARY

The present invention is directed to an apparatus, systems, and methods to optimize hemodynamics within a patient's heart, e.g., in order to improve exercise capacity. More particularly, the present invention is directed to implantable devices that optimize intra-cardiac filling pressures; and to systems and methods for using such devices.

The device may measure and/or control the amount of blood flowing in a direction opposite to the normal direction (regurgitation). By controlling regurgitation, the device can manipulate and optimize left-sided filling pressures. Furthermore, the device may pace the heart (increase the heart rate) for therapeutic and diagnostic purposes. For example, in one embodiment, the device may gradually adjust the heart rate and/or the regurgitant volume and measure changes in pressure measurements and/or blood flow in order to identify optimal device function. By controlling the heart rate and monitoring changes in flow and pressure, the device may estimate the optimal filling pressures of the left ventricle. The device may then optimize left-sided filling pressures by adjusting the amount of regurgitation. Seemingly counterintuitive, cardiac output may be maintained and symptoms may be improved by inducing regurgitation in a controlled and monitored system.

In patients with significant biventricular discordance, more regurgitation can be induced to maintain lower left-sided filling pressures. In patients with more balanced ventricular function, the amount of controlled regurgitation may be less. Furthermore, the amount of regurgitation and/or heart rate can be changed during exercise in order to improve exercise capacity. Therefore, the device may be able to optimize left-sided filling pressures at baseline and with exertion.

In another embodiment, the heart rate is titrated simultaneously to optimize cardiac output and left-sided filling pressures. While this device may also help patients with heart failure, many embodiments of this application are directed at patients who have no evidence of heart failure. In these patients, the systems and methods herein may prevent hyperventilation and/or chronotropic incompetence that may occur as a result of an elevation in pulmonary pressures and/or left-sided filling pressures and improve exercise capacity.

In some cases, the system may accept a reduction in cardiac output if there is evidence or suspicion the higher pressures are affecting exercise capacity, e.g., by monitoring respiratory patterns or input from the patient and/or caretakers. In other cases, the patient may signal to the device any symptoms that they are having. In one embodiment, the device may measure minute ventilation. Therefore, the device may monitor parameters of patient symptoms and manipulate heart rate and the regurgitant volume accordingly. The device may create a feedback loop where heart rate and regurgitation are adjusted while measuring changes in left-sided filling pressures and/or parameters of exercise capacity. Furthermore, pressure sensors are susceptible to drift, such that changes in pressure may be monitored more easily than absolute pressure. Therefore, in some embodiments, the device measures changes in pressure, rather than absolute pressure. In another embodiment, the device may monitor for changes in both stroke volume and pressure data in order to determine where the patient is on their pressure-stroke volume relationship curve. This data may be used to guide the function of both the pacing and regurgitating function.

In another embodiment, the system may permit blood to travel from the left atrium to the right atrium. The amount of blood flow through this shunt may be adjustable in order to optimize hemodynamics. For example, at rest, the size of the shunt may be small or closed. However, during exertion, the shunt size may be increased in order to compensate for rapidly rising filling pressures.

The device may also facilitate diuresis in patients with volume overload and/or heart failure. In these patients, increasing cardiac output may improve renal perfusion and urine output, thereby improving volume status. In order to most effectively titrate heart rate, the systems and methods herein may monitor both intra-cardiac pressures and cardiac output. Increasing the heart rate in these individuals may increase cardiac output; however, this may also increase left-sided filling pressures. Elevations in left-sided filling pressures can cause breathlessness to the patient. By increasing both heart rate and causing some regurgitation, the device may facilitate diuresis without causing shortness of breath. If the device determines total body volume is increased, the device may increase cardiac output while preventing elevations in left-sided filling pressures. By monitoring and preventing this rise in pulmonary and/or left-sided filling pressures with exertion, the device may prevent exertional exercise hyperventilation. Similarly, this device may improve sleep apnea caused by elevated filling pressures. Finally, this device may increase chronotropic incompetence that may occur as a result of elevated filling pressures.

In another embodiment, controlling the heart rate may be used for monitoring. For example, the heart rate will affect filling pressures and stroke volume. By monitoring changes in flow and/or pressure, the device may estimate intravascular volume based on the affect heart rate has on hemodynamics. The pacing function may include pacing the right ventricle, right atrium, and/or the left ventricle from the coronary sinus. The pacing function may also be combined with the pressure sensor. For example, a pressure sensor may be placed in the coronary sinus, with or without an occlusion, so that the pressure of the left ventricle may be estimated. This component may be combined with the pacing function so that the heart may be paced from this location.

In another embodiment, the waveform of the pressure tracings, with or without an estimate of stroke volume, may be used to estimate left-sided filling pressures. In other embodiments, optimal heart rate and/or regurgitant volume may be adjusted based on flow measurements. For example, if the regurgitant volume is increased (which will lower left-sided filling pressures), but the measured the cardiac output does not change, this finding may suggest that the higher filling pressures were not contributing to cardiac output. Therefore, the device may optimize filling pressures even without monitoring pressure directly.

In accordance with another exemplary embodiment, the apparatus, systems, and methods herein may determine an elevation in total body blood volume and optimize cardiac output by adjusting heart rate. Volume status may be interpreted by traditional metrics, such as by measuring thoracic impedance or pressure sensors, in addition, the device may estimate volume status by measuring changes in left-sided blood pressure and/or stroke volume in response to changes in heart rate or regurgitant volume. The system may estimate the patient's filling pressure to stroke volume relationship of the left ventricle by measuring changes in response to perturbations in the system. This may enable the device to effectively create a feedback or closed-loop system. Aspects of the feedback loop system may be adjusted by outside or remote communication; however, the device may be able to regulate its own function through this feedback system. For example, the optimal filling pressures may change over time. The device may estimate the optimal filling pressures based on flow responses or estimates of exercise capacity. The device may also monitor for sleep apnea based on respiratory patterns and change function in response. In another embodiment, the device monitors patient position (standing up versus laying down) and adjust function accordingly.

In one embodiment, a device changing the cross-sectional area to the pulmonary artery is implanted within a patient's body. This device is able to decrease left-sided filling pressures by increasing right ventricular afterload (and thereby reduce right ventricular stroke volume). In another embodiment, a device that monitors and reduces the effective size of the right atrium is implanted. By reducing the blood pooling reservoir function of the right atrium, the effective right ventricular end-diastolic pressure is reduced with each heart beat-therefore reducing left-sided filling pressures. In yet another embodiment, the function of the tricuspid valve or pulmonic valve is impaired, such that regurgitant flow is controlled and titrated in efforts to optimize left-sided filling pressures. In yet another embodiment, the size of a shunt connecting the left and right atrium (by placing a shunt or tube within the interatrial septum) may be placed to optimize left ventricular end diastolic pressure (LVEDP). In yet another embodiment, sensors capable of measuring blood oxygen sensors are utilized to estimate cardiac output and/or oxygen consumption.

Mechanical movement may perform these methods, such as through an electric motor. In another embodiment, the device may affect blood flow or cardiac function by pumping a gas or fluid into various structures, for example, a balloon-like structure. In these embodiments, changing the size and/or orientation of various structures affect vessel cross-sectional area, venous capacitance, and/or induce drag on blood flow fluid mechanics.

The device may be attached or respond to pressure measurements obtained in certain locations of the heart or body. Alternatively, the device may determine function based on measures of autonomic tone or heart rate. In one embodiment, the number of impulses per minute (or frequency of bursts), measured in nerve structures (for example, the phrenic nerve) are monitored and utilized to guide device function. The device may also measure stroke volume of the left or right ventricle. By measuring parameters indicative of cardiac output and/or intra-cardiac filling pressures, the device may be able to determine the optimal left-sided filling pressures to maximize cardiac output while minimizing patient symptoms. The device then creates a feedback loop, or closed loop system, whereby the device monitors pressure or stroke volume; and optimizes heart rate, filling pressures, and/or cardiac output.

In addition, other exemplary embodiments of the device may include the ability to report left-sided filling pressures to the patient and/or clinical care team in order to optimize medication therapy. In one embodiment, a tube is placed connecting the right ventricle to the right atrium. A flow occlusion element is placed inside the tube to control the regurgitant flow retrograde through the tube.

In another embodiment, the tricuspid tube connecting the right atrium and right ventricle is a self-expanding metal alloy (such as Nitinol) lattice frame with a Dacron or PTFE graft attached to the inside. The design of this tube is such that the outer rim is made of a thicker reinforced rubber, elastomer, or other plastic, with the inner portion a low compliance design to allow for easy distensability. This easily distendable inner portion alongside the reinforced outer portion may allow the balloon to have an increasingly smaller open inner diameter as it is inflated. At full inflation, it may result in near occlusion of the tube with a resultant drop in regurgitant blood flow. When pressures inside the heart increase, flow through the tube is permitted to increase in order to normalize intra-cardiac filling pressures. In another embodiment, the device prevents optimal valve function, e.g., by presenting leaflet coaptation. By affecting valve function, blood flow may travel in a retrograde direction (backwards).

In another exemplary embodiment, flow through the tube is controlled by a micro-hydraulic pump. In another embodiment, the tube includes a one-way valve, where the integrity/function of the valve is controlled in order to control regurgitated blood flow through the tube. The device may be positioned in the inferior vena cava, right atrium, right ventricle, along the tricuspid annulus, or in the interatrial septum. The device may function by preventing valve leaflets from optimal coaptation, and therefore, the size, orientation, or shape may be changed by the device in order to induce regurgitation and decrease left-sided filling pressures.

Some embodiments may use pressure sensors to guide heart rate and regurgitant volume. In other embodiments, left-sided filling pressures are estimated by monitoring trends in stroke volume in response to changes in heart rate and/or regurgitant volume. For example, if the relative stroke volume is not reduced (and sustained) with an increase in regurgitant flow, this finding suggests the reduction in left-sided filling pressures (in response to the increased regurgitation) is not affecting cardiac output. Therefore, this may signal to the device that the patient is volume-overloaded.

In other embodiments, stroke volume and/or cardiac output is measured using impedance changes from a plurality of electrodes, piezoelectric sensors, ultrasound sensors, oxygen saturation sensors, temperature sensors, and/or pressure sensors. In another embodiment, flow is estimated by reviewing pressure sensor waveforms. Furthermore, since pressure sensors are prone to drift, the device can determine function by measuring changes in pressure (as opposed to absolute pressure measurements).

In another embodiment, the regurgitation component is connected to a pacing or defibrillator lead in order to treat conduction disease or defibrillate the heart. In addition, the pacing lead may be able to monitor heart rates. In yet another embodiment, the pacing lead may also include pressure sensors to determine the pressure inside the right ventricle. In yet another embodiment, the lead may include electrodes capable of sensing electrical impedance, and, throughout the heart cycle, the device may estimate the stroke volume of the right ventricle. In yet another embodiment, the component controlling regurgitation may include a one-way valve.

In another embodiment, if the device determines the patient is volume overloaded, the device may attempt to increase cardiac output. Therefore, the device may attempt to increase cardiac output to facilitate diuresis and decrease the total body volume level. Since increasing heart rate may increase left-sided filling pressures, the device may induce regurgitation simultaneously. By limiting the elevation in left-sided pressures, the device can minimize the shortness of breath the patient may experience with the higher heart rate. In this embodiment, the device will encourage diuresis while minimizing symptoms of heart failure.

In yet another embodiment, the device performs diagnostic tests on the patient. For example, the device may gradually change the heart rate and measure changes in the stroke volume and/or blood pressure. Furthermore, the device may change both the heart rate and the pressure gradient or regurgitant volume in order to identify the cardiac function under a variety of loading conditions. This information may be combined with sensors corresponding to patient activity or exertion level.

Optionally, the systems and methods herein may also communicate to the patient their total body blood volume status and/or help manage their medical management. In this embodiment, the device may communicate sensor recordings outside of the body. The device may then be an agent to help advise the patient on medication. For example, when intra-cardiac pressures increase, the device, in addition to facilitating diuresis, the device may communicate to the patient or the patient's health care professionals, that a change in medication or therapy is advised. Therefore, the device may help the patient obtain optimal volume status. Furthermore, even when the patient has the optimal filling pressures at rest, these patients typically have significant elevations in pulmonary pressures and left-sided filling pressures. Therefore, in addition to helping the patient optimize their filling pressures, the device may still control regurgitation function in order to prevent elevated filling pressures during exercise. Therefore, the device may help optimize the patient chronically over time and more acutely with changes in activity. In accordance with still another embodiment, systems and methods may be provided that allow for wireless communication. Therefore, sensors may be implanted separately from the rest of the apparatus/device that communicate to each other.

In addition or alternatively, the apparatus, systems, and methods may be responsive to patient activity to optimize cardiac performance and intra-cardiac pressures to improve exercise capacity. Optionally, the system may include a sensor that reflects patient movement or activity. When this sensor suggests, for example, that the patient is active, the device may increase cardiac output in order to deliver more blood to the body. In yet another embodiment, the device may change the target level of the left-sided filling pressures, that is, when the device senses the patient is moving or exerting themselves, the optimal left-sided filling pressures may change in order to optimize hemodynamics. Similarly, the device may sense when the patient is sleeping and change function accordingly.

In accordance with still another embodiment, the system and methods may gradually adjust the regurgitant component and/or heart rate in order to create pressure-cardiac output relationships. Analysis of these relationships can then be used to guide device functioning. In another embodiment, systems and methods may be provided to create retrograde flow. This regurgitation feature may include one or more shunts, balloons, orifices, valves, and the like, e.g., to facilitate blood to flow from the right ventricle to the right atrium.

In yet another embodiment, the regurgitation component may be pressure sensitive. For example, when the pressure within the right ventricle exceeds a certain pressure, the regurgitant component permits blood to regurgitate from the right ventricle to the right atrium. This mechanism prevents pulmonary pressures from exceeding a certain value. Furthermore, in another embodiment, this system may not require a processor or controller. For example, the regurgitation component may mechanical deform in response to a high pressure gradient between two areas, such as, the right atrium and right ventricle.

In another embodiment, the material may be comprised of fabric material, such as polyester, nylon, or polypropylene. In other embodiments, the material may be made of stainless steel, nitinol, titanium, cobalt alloys, cobalt-chromium-nickel allows, MP35N, polymeric material, or any other suitable biocompatible material. The regurgitant member may be self-expanding, balloon expanding, or a shape-memory material. In another embodiment, aspects of the device may be made from tubing or wire. In yet another embodiment, the regurgitant component may be made of porcine or donor material, such as mammalian veins or heart valves. In other embodiments, the regurgitant component may include elastomeric materials, such as silicone or perfluorocarbon elastomers.

Other aspects and features of the present invention will become apparent from consideration of the following description taken in conjunction with the accompanying drawings.

BRIEF DESCRIPTION OF THE DRAWINGS

The invention is best understood from the following detailed description when read in conjunction with the accompanying drawings. It will be appreciated that the exemplary apparatus shown in the drawings are not necessarily drawn to scale, with emphasis instead being placed on illustrating the various aspects and features of the illustrated embodiments.

DETAILED DESCRIPTION OF THE EXEMPLARY EMBODIMENTS

Figure 1:
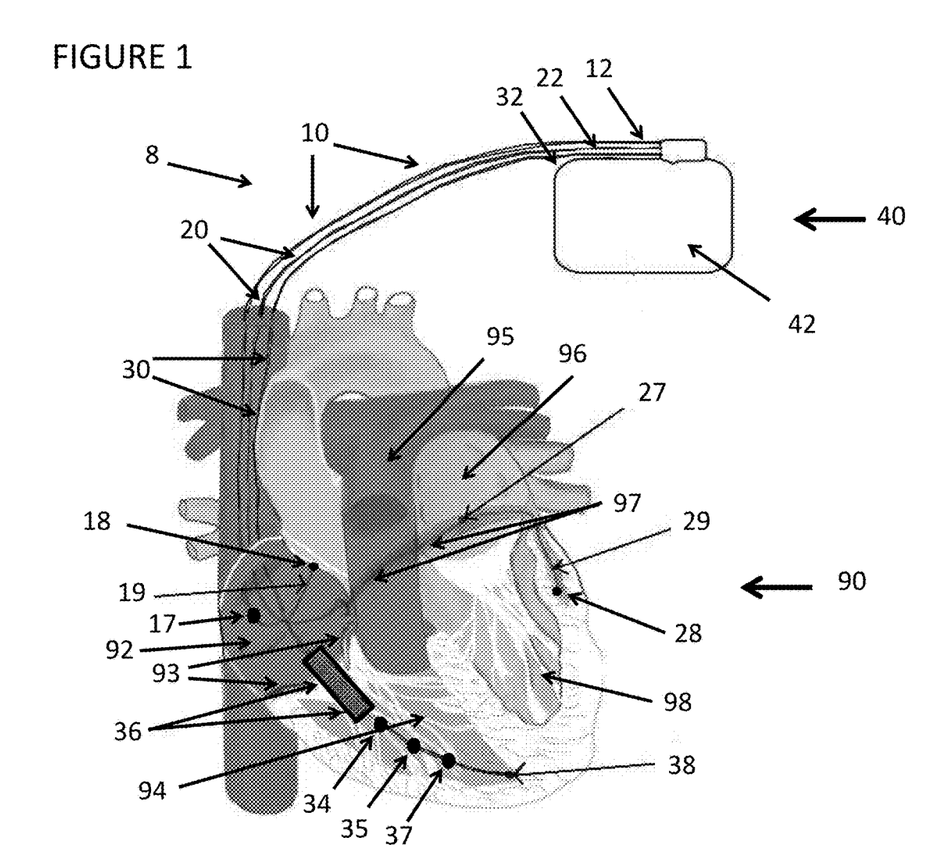
FIG. 1 shows an exemplary embodiment of a system, e.g., an implantable pressure regulator/pacemaker/defibrillator, implanted within a patient's body.

FIG. 1 shows an exemplary embodiment of a system 8 including a pressure regulator/pacemaker/implantable cardio-defibrillator (ICD) with specialized leads going into a patient's heart 90, e.g., for practicing the exemplary systems and methods described elsewhere herein. In the embodiment shown in FIG. 1, the system 8 includes a controller 40 including a housing 42 sized and/or otherwise designed to be implanted within the patient's body. The housing 42 of the controller 40 is connected to several leads 10, 20, 30 that are designed to be implanted into the patient's heart 90.

For example, as shown, a first lead 10 may include a proximal end 12 coupled to the housing 42 and a second end sized for introduction into the patient's heart 90, e.g., into the right atrium 92. The first lead 10 may have a distal end 19 carrying a sensor and/or electrode 18 for sensing electrical activity (depolarizations) and/or pacing the right atrium 92, as programmed. In addition, the distal end 19 of the first lead 10 may include one or more features, e.g., a screw tip or other anchor (not shown) on its distal tip for securing the distal end 19 relative to the right atrium 92 or left atrium 96. One or more wires or other conductors may extend from the distal end 16 to the proximal end 12 to communicate the signals from the sensor 18 to the controller 40.

Similarly, a second lead 20 may include a proximal end 22 coupled to the housing 42 and a second end sized for introduction into the patient's heart 90, e.g., into the right atrium 92 through the coronary sinus 97 or other vein of the heart 90. The second lead 20 may include a sensor or electrode 27 designed to sense or measure pressure in the left atrium 96. In addition, the second lead 20 may include a distal end 29 carrying an additional sensor or electrode 28 for sensing or measuring pressure located within the distal coronary sinus 97, which may be reflective of left ventricle 98 pressures. Similar to the first lead 10, the second lead 20 may include one or more features, e.g., a screw tip or other anchor (not shown), on the distal tip to secure the distal end 29 within the patient's heart 90, e.g., within the coronary sinus 97, similar to pacing leads. Alternatively, the first and second leads may be provided on a single device with a branch distal end (not shown), similar to embodiments described in the applications incorporated by reference herein.

Additionally, there may be a third lead 30 with a proximal end 32 to couple the lead 30 to the housing 42. The third lead 30 may include a second end sized for introduction into the patient's heart 90, e.g., into the right atrium 92, through the tricuspid valve 93 and into the right ventricle 94. The third lead 30 includes a distal end, which may include an electrode and/or sensor 38 designed to sense electrical activity or deliver electrical energy to stimulate the right ventricle 96.

Similar to the first lead 10 and second lead 20, the third lead 30 may include one or more features, e.g., a screw tip or other anchor (not shown), on the distal tip to secure the distal end within the patient's heart 90, e.g., into the wall of the right ventricle 94, similar to typically used pacing leads. The third lead 30 may sense and pace electrical activity occurring in the right ventricle 94. In addition, the third lead 30 may include electrodes 34 and 35 designed to sense electrical capacitance at several points in time throughout the cardiac cycle to estimate the stroke volume of the right ventricle 94. For example, changes in impedance throughout the cardiac cycle may be used to estimate volume changes in the right ventricle. Even with drift in electrical signals over time, these measurements can determine changes in volume changes which may be used to guide the pressure gradient or regurgitant volume.

In addition, the third lead 30 may include a tube-like structure 36, designed to permit controlled flow to travel from the right ventricle 94 to the right atrium 92. The regurgitating flow traveling through the tube decreases the forward flow through the pulmonary artery, and ultimately the left atrium 96 and left ventricle 98. This tube-like structure may include one or more flow sensors, e.g., a rotating sensor, magnetic flux sensors, and/or other flow sensors such that retrograde flow may be measured. By combining volume changes in the right ventricle and retrograde flow measurements, stroke volume (and therefore cardiac output) may be estimated, especially relative changes in stroke volume. Alternatively, sensors measuring oxygen saturation or directly measuring flow, e.g., through the pulmonary artery 95, may be included to estimate stroke volume of the right ventricle 94.

In some embodiments, measuring changes in flow in response to changes in a pressure gradient or regurgitant volume, optimal heart rate and/or regurgitant volume may be estimated. In other embodiments, pressure waveforms from pressure sensors from the right ventricle 94 and/or the pulmonary artery 96 may be analyzed to better estimate left-sided filling pressures, e.g., the end diastolic filling pressure of the left ventricle 98. The pressure waveforms may by analyzed by identifying the pulmonary artery systolic, diastolic, and/or mean pressure in order to estimate left-sided filling pressures.

One or more pressure sensors may be placed at desired locations, e.g., in the left atrium, on the interatrial septum, or in the coronary sinus 97 (with occlusion to optimize pressure recordings), in order to estimate left-sided filling pressures. In addition or alternatively, one or more pressure sensors may be placed in the right atrium 92, right ventricle 94, right ventricular outflow track, or pulmonary artery 95. By combining flow measurements with pressure sensors within the blood system prior to the lungs, filling pressures from the left atrium and/or left ventricle 98 may be estimated. The waveform analysis may include absolute pressures and/or the slope or change in pressure (tao) during the cardiac cycle.

Figure 2:
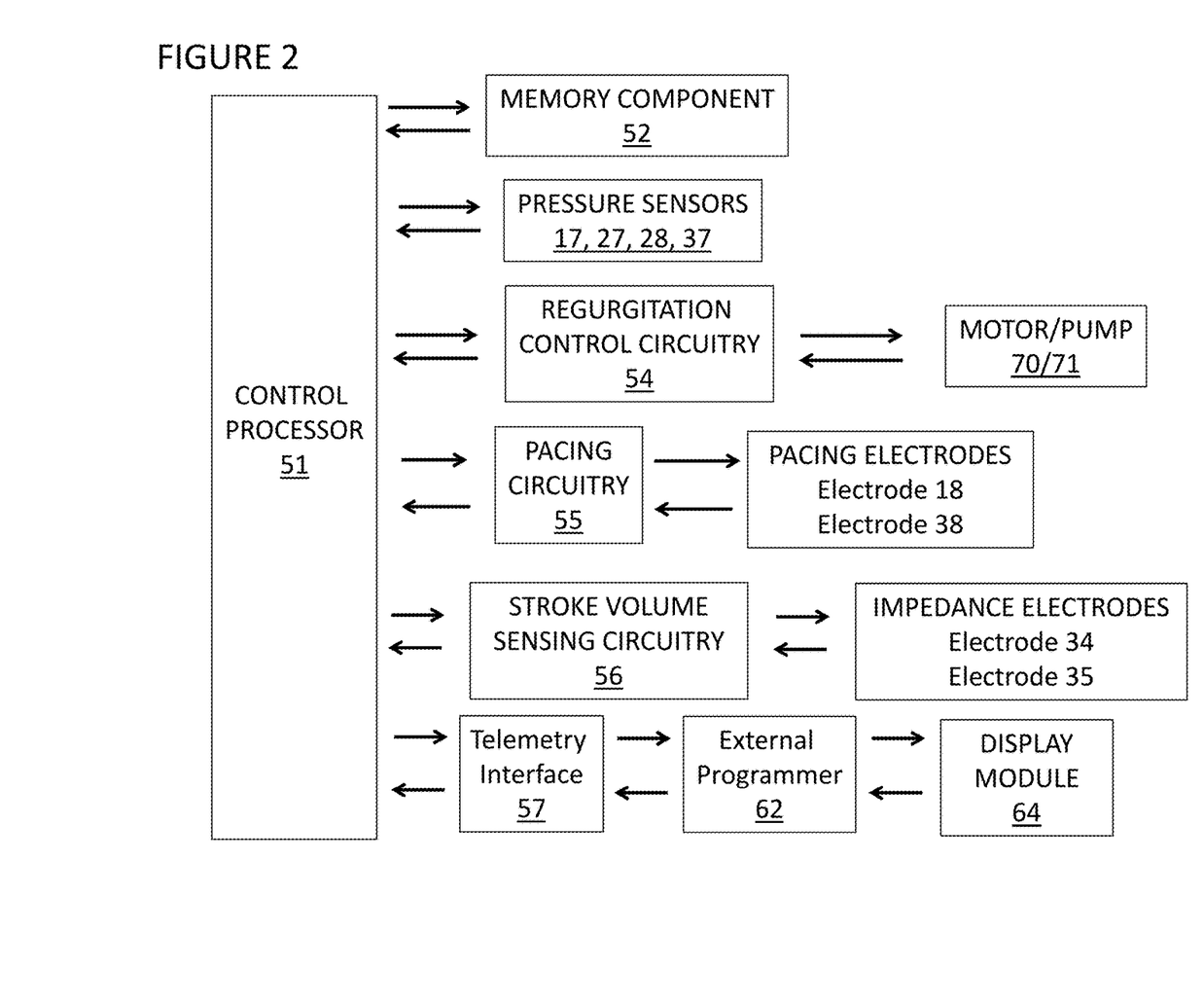
FIG. 2 is a functional block diagram of the circuitry of the system of FIG. 1.

FIG. 2 shows a simplified functional block diagram of one embodiment of the components located within and connected to the controller 40. The components include a control processor 51, which receives input information from various components in order to determine the function of the different components to treat the patient. The control processor 51 is connected to a memory component 52, pressure sensors (17, 27, 28, and 37), regurgitation control circuitry 54, pacing circuitry 55, stroke volume sensing circuitry 56, and a telemetry interface 57. The pacing circuitry 55 connects to the electrodes, for example, electrodes 18 and 38. These connections allow for multiple capacities to sense electrical activity (such as myocardial depolarizations), deliver pacing stimulations, and/or deliver defibrillation or cardioversion shocks. The regurgitation control circuitry is connected to a motor 70 or pump 71 to affect blood flow 36. The stroke volume sensing circuitry is connected to electrodes, for example electrodes 34 and 35. These electrodes sense change in impedance values at periods of the cardiac cycle to estimate stroke volume. Optionally, the control processor 51 is connected to a telemetry interface 57. The telemetry interface may wirelessly send and receive data from an external programmer 62 which is coupled to a display module 64 in order to facilitate communication between the control processor 51 and other aspects of the system external to the patient.

Figure 3:
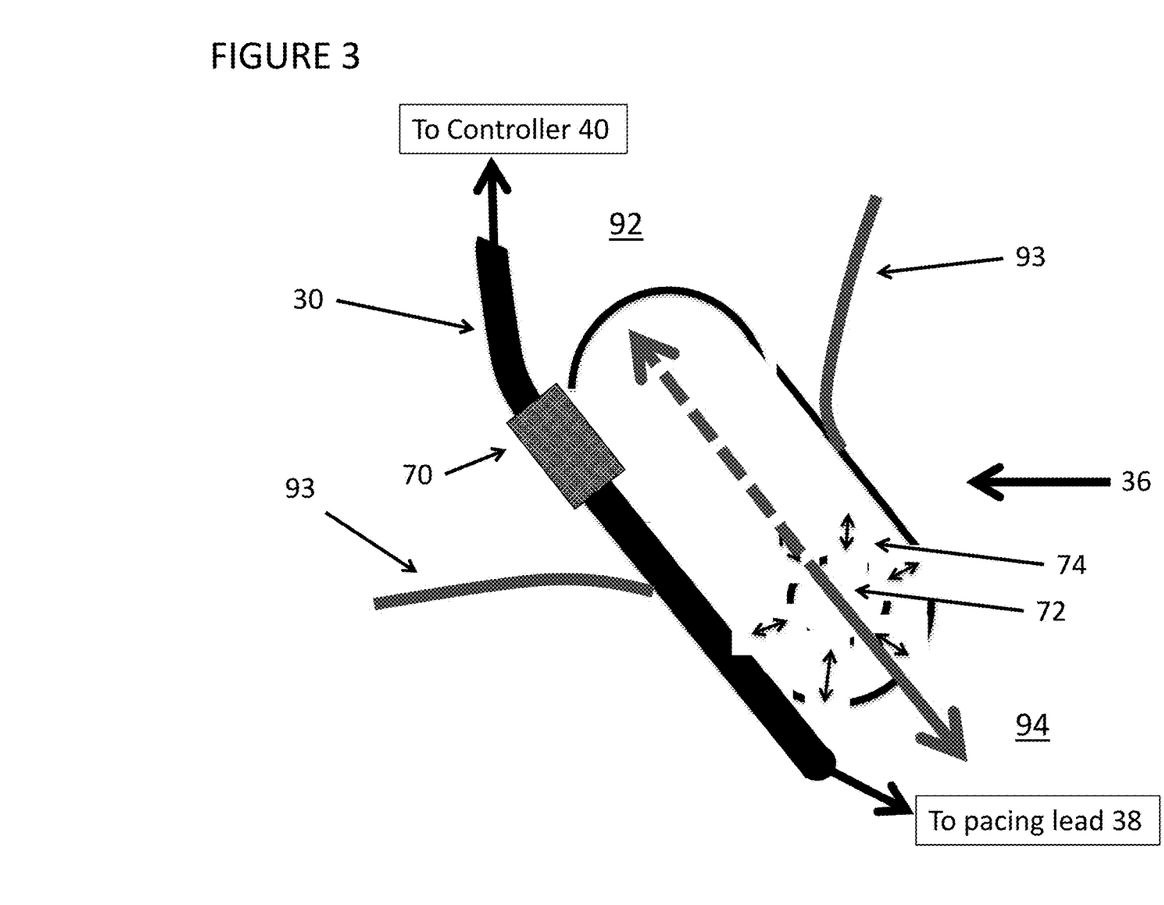
FIG. 3 shows an exemplary embodiment of a device for controlling flow from the right ventricle to the right atrium within a heart.

FIG. 3 shows an exemplary embodiment of a lead 30 including a regurgitant component that may be implanted within a patient's heart 90, e.g., to control flow of blood from the right ventricle 94 to the right atrium 92. In this embodiment, the lead 30 carries a tube device 36 designed to be placed across the tricuspid valve leaflets 93 to provide controllable regurgitation between the right ventricle and the right atrium (not shown). In an exemplary embodiment, the tube device 36 has an inner tubular core 72 defining a lumen or passage capable of transmitting blood from the right ventricle 94 to the right atrium 92. The tube device 36 is connected to a motor 70 able to change the size of the inner core 72 by changing the size or orientation of an annular outer body 74 of the tube surrounding the inner core 72. Alternatively, the tube device 36 may communicate with a micropump (not shown), e.g., within the controller 40, able to pump a liquid or gas substance into the outer body 74 of the tube. The tube device 36 is connected to the controller 40 for controlling operation of the tube device 36, and is mounted on the lead 30 proximally to the pacing lead 38, e.g., secured in the apex of the right ventricle 94. By adjusting the size of the inner core 72, the controller 40 is able to control the amount of regurgitated blood traveling from the right ventricle 94 to the right atrium 92. This blood flow shunts blood away from the pulmonary artery 95; and ultimately will decrease the pressure in the left atrium 96 and left ventricle 98.

In another embodiment, the regurgitation component may be pressure sensitive. For example, when the pressure within the right ventricle exceeds a certain pressure, the regurgitant component permits blood to regurgitate from the right ventricle to the right atrium. This mechanism prevents pulmonary pressures from exceeding a certain value. Furthermore, in another embodiment, this system may not require a processor or controller. For example, the regurgitation component may mechanical deform in response to a high pressure gradient between two areas, such as, the right atrium and right ventricle.

In an exemplary embodiment, the tube device 36 may be an annular balloon device formed from desired materials. For example, the material may be comprised of fabric material, such as polyester, nylon, or polypropylene. In other embodiments, the material may be made of stainless steel, nitinol, titanium, cobalt alloys, cobalt-chromium-nickel allows, MP35N, polymeric material, or any other suitable biocompatible material. The regurgitant member may be self-expanding, balloon expanding, or a shape-memory material. In another embodiment, aspects of the device may be made from tubing or wire. In yet another embodiment, the regurgitant component may be made of porcine or donor material, such as mammalian veins or heart valves. In other embodiments, the regurgitant component may include elastomeric materials, such as silicone or perfluorocarbon elastomers.

Figure 4:
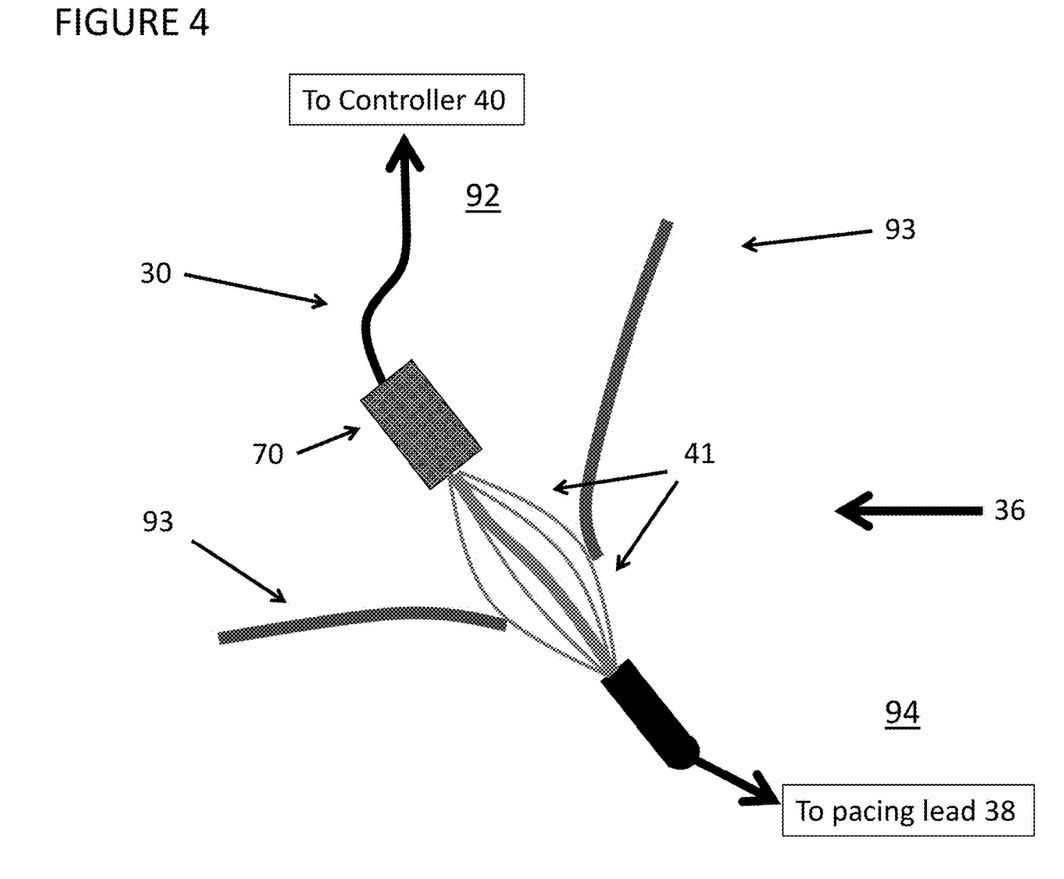
FIG. 4 is another exemplary embodiment of a device for controlling flow from the right ventricle to the right atrium.

FIG. 4 shows an additional exemplary embodiment of a lead 30 including a movable structure 41 that may be implanted within a patient's heart 90, e.g., to control flow of blood from the right ventricle 94 to the right atrium 92. This lead 30 may be connected to the pacing electrode 38 in the right ventricle 94 to pace the heart (e.g., to increase the heart rate). The lead 30 carries the movable structure 41 at a desired location, e.g., around the outside of the lead 30. This movable structure 41 may be connected to a motor 70, such that changes in shape and/or orientation of the movable structure 41 will affect or prevent leaflet coaptation from the tricuspid valve 93. In an exemplary embodiment, the movable structure 41 may have several spindle-like structures made up of or coated with biocompatible material. For example, the motor 70 may be mounted on the lead 30 such that the motor 70 may move towards or away from the tip of the pacing lead 38 such that the spindles increase or decrease in diameter. Therefore, the motor 70 may cause radial expansion in order to induce regurgitation. In this and other configurations, the controller 40 may induce or control blood to regurgitate from the right ventricle 94 to the right atrium 92.

Figure 5:
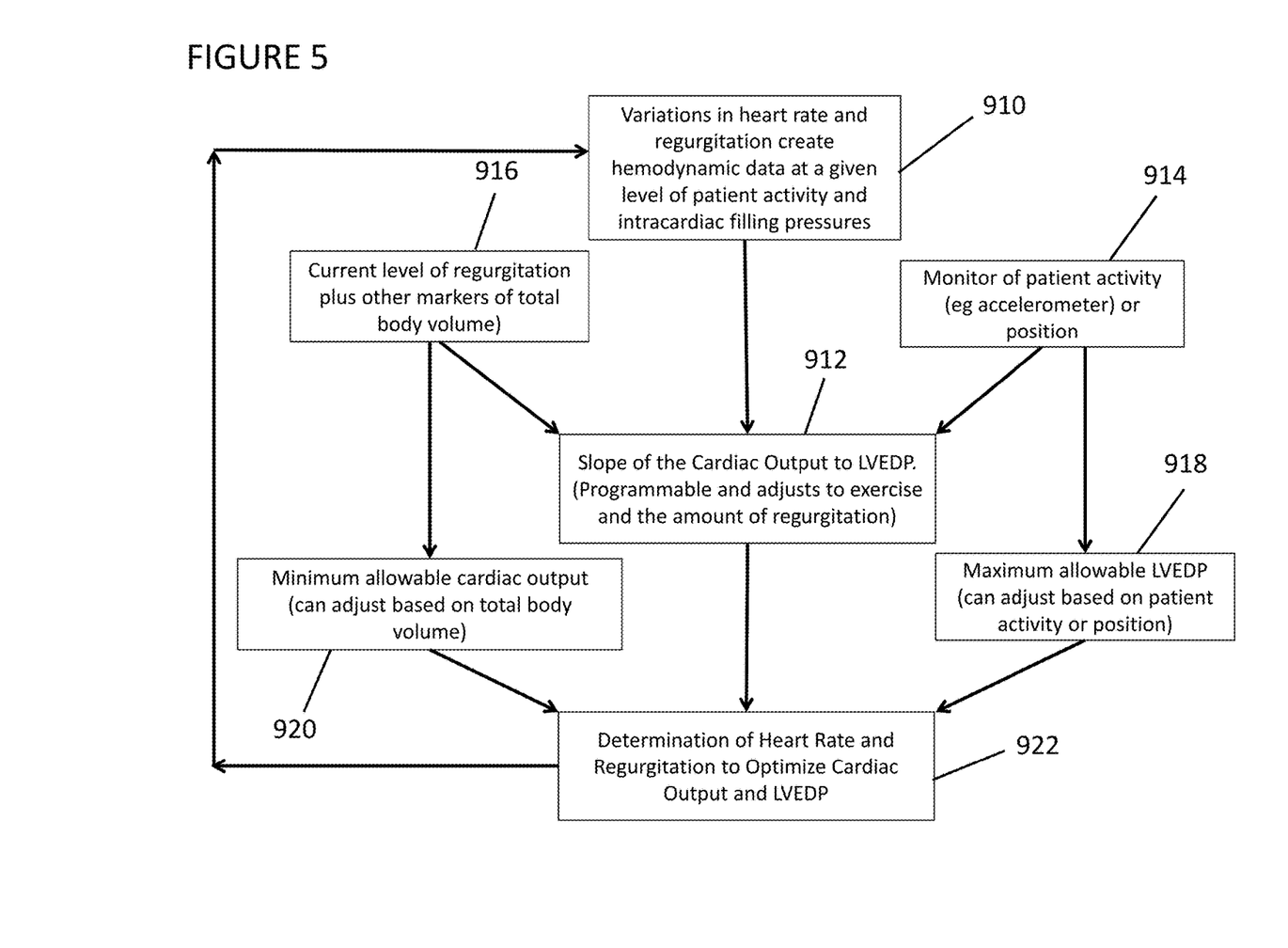
FIG. 5 is a flow chart showing an exemplary method for determining the optimal heart rate and regurgitant volume based on measurements and programmable aspects of a system implanted within a patient's body.

Turning to FIG. 5, an exemplary method is shown for determining optimal heart rate and/or regurgitant volume, e.g., using any of the systems described elsewhere herein. The controller of the system may operate the regurgitant volume and other components to enable the desired data to be acquired and calculations to be performed. Variations in heart rate and regurgitant volume are used in order to estimate the relationship between left-sided filling pressures and cardiac output. For example, at step 910, heart rate and regurgitant volume may generate hemodynamic data at a given level of patient activity and intra-cardiac filling pressures.

At step 912, the controller may then use the slope of this relationship to determine the optimal left-sided filling pressure and cardiac output. Optionally, at step 914, an accelerometer implanted in the patient's body, e.g., within the housing 42 of the controller 40 shown in FIG. 1, may be used to identify the patient's level of activity. For example, the controller 40 may acquire data from the accelerometer indicating that the patient is resting (e.g., no substantially signals from the accelerometer) or active.

In addition, at step 916, the controller 40 may identify the current level of regurgitation, which may provide an estimate of the total body volume of the patient. In another embodiment, the device may measure if the patient is sleeping or has evidence of sleep apnea and change function based on the identification of said occurrence.

At step 918, the controller 40 may also determine the maximum allowable left-sided filling pressure and minimum cardiac output allowable. These values may also be dependent on the level of patient activity and/or the total body blood volume. That is, when the patient is at an increased level of activity, the controller may accept a higher maximum of left-sided filling pressure.

Optionally, the device may determine or have pre-programmed levels of minimum allowable cardiac output (step 920). For example, the device may identify a rise in total body volume when the cardiac output falls below this threshold. Therefore, the device may identify a level of cardiac output not sufficient to satisfy the demands of the body.

Similarly, the device may identify a left-sided filling pressure, e.g., the left ventricular end diastolic pressure, where the patient cannot maintain activity, or where the device measures a rapid increase in ventilation (step 918). Therefore, the device may identify a certain LVEDP (or rapid change in LVEDP) that results in shortness of breath. Therefore, the device may have a programmed (or monitored or adjustable) LVEDP threshold such that the device does not allow this pressure to go higher. The device may set this LVEDP even if a higher pressure increases cardiac output. This setting may be useful because left-sided filling pressures may be more predictive of exercise capacity rather than cardiac output. Therefore, while the device may be limiting cardiac output, the reduction in left-sided filling pressures actually improve patient quality of life.

At step 922, these values are then incorporated into an algorithm by the controller 40. These values are then gradually adjusted (feedback loop) back to step 910 in order to identify the optimal settings to optimize patient hemodynamics and quality of life.

Once calibrated, regurgitant volume and heart rate may be anticipated based on patient activity and intra-cardiac pressures in order to optimize filling pressures and/or cardiac output. Over time, the decreased left atrium and left ventricle filling pressures may lead to beneficial myocardial remodeling. This may improve myocardial function and/or decrease arrhythmias and/or ectopic beats.

Figure 6:
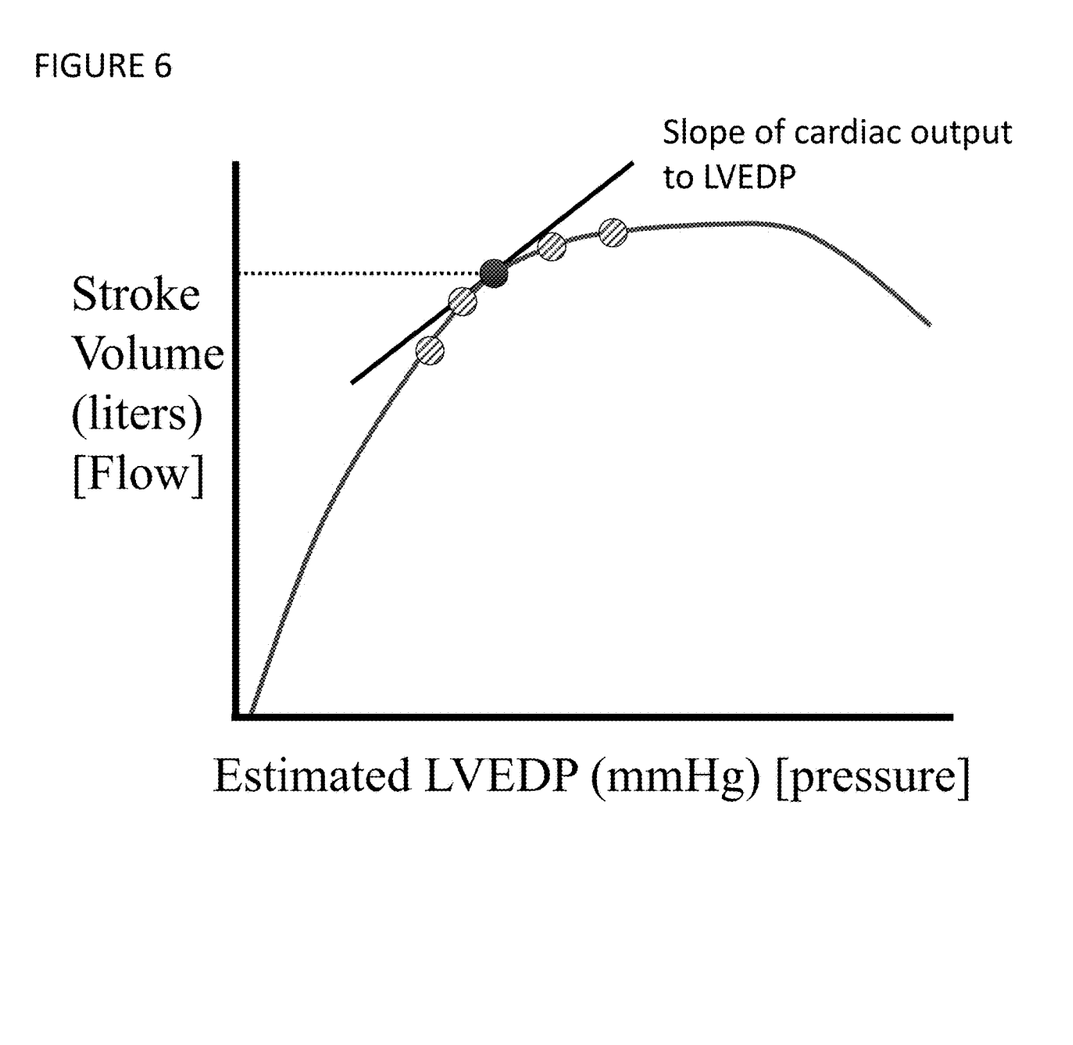
FIG. 6 is a graph showing the relationship between the estimated left-sided filling pressures and estimates of cardiac output illustrating an exemplary method for using the slope of this relationship to determine the optimal heart rate and regurgitation component.

Turning to FIG. 6, this figure illustrates an exemplary method of using the pressure/volume relationship to guide the heart rate and regurgitation components of the device. In response to changing volume status, heart rate, adrenergic level, and regurgitant volume, the device may monitor both estimated change in pressure and estimated change in stroke volume. In other embodiments, the device may attempt to measure absolute pressure and/or stroke volume. Therefore, the device may estimate the how increasing the heart rate and regurgitation will affect cardiac output and filling pressures.

For example, when filling pressures rise without a concomitant increase in stroke volume, the slope of this relationship suggests raising the filling pressure higher will contribute to shortness of breath and hyperventilation without improving forward flow. Therefore, the slope of this relationship may be used to guide heart rate and the component that influences regurgitation. In addition, the device may estimate optimal resting filling pressures to guide volume status. For example, if the device suggests the patient is volume-overloaded, the device may increase cardiac output to favor renal perfusion and diuresis. The device may simultaneously minimize how high the LVEDP may raise to limit symptoms. Alternatively, the device may communicate to the patient or patient's healthcare team that a medication adjustment should be done to help optimize patient hemodynamic status.

The device may also combine the LVEDP measurement with hemodynamic monitors during exertion, sleep, or various kinds of movement. In other embodiments, the device may use oxygen saturation, pH, respiratory rate, and/or lactate levels (or a combination) in order to determine the optimal filling pressure. For example, some patients require an LVEDP greater than 30 mmHg to maintain stroke volume. However, other patients maximize their stroke volume when the LVEDP reaches 10 mmHg. Therefore, by determine the response of stroke volume and/or cardiac output at various filling pressures (LVEDP), the device may identify the optimal LVEDP. In another embodiment, the LVEDP, where there is excess hyperventilation, acidosis, or lactate accumulation, may be identified as the maximum filling pressure to optimize patient exercise capacity.

It will be appreciated that elements or components shown with any embodiment herein are exemplary for the specific embodiment and may be used on or in combination with other embodiments disclosed herein.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

We claim:

1. A system configured to be implanted in a patient's body to monitor and/or treat the patient, the system comprising:
   at least one sensor configured to provide sensor data that corresponds to a blood pressure within or near the patient's heart;
   at least one adjustable component designed to cause regurgitation where blood flows in a direction opposite to the normal direction within a region of the patient's heart; and
   a controller configured for adjusting the function of the at least one adjustable component based at least in part on sensor data from the at least one sensor.

2. The system of claim 1, further comprising a pacing component coupled to the controller capable of at least one of sensing or pacing a chamber of the heart.

3. The system of claim 2, further comprising an activity sensor coupled to the controller configured to identify patient activity coupled to the controller.

4. The system of claim 3, wherein the activity sensor comprises one of an accelerometer or a sensor sensitive to minute ventilation.

5. The system of claim 2, further comprising one or more sensors coupled to the controller configured to measure data that corresponds to blood flow or blood volume.

6. The system of claim 5, wherein the one or more sensors comprise one of a blood oxygen sensor and a plurality of electrodes coupled to the controller configured to measure changes in electrical impedance that correlate with changes in blood volume.

7. The system of claim 2, wherein the controller is configured to adjust both the pacing component and the adjustable component in response to sensor data from the at least one sensor.

8. The system of claim 1, wherein the at least one sensor is configured to be located in one of the patient's pulmonary artery, right atrium, superior vena cava, inferior vena cava, right ventricle, left atrium, left ventricle and coronary sinus.

9. The system of claim 1, further comprising a second pressure sensor coupled to the controller configured to measure pressure proximal to the at least one adjustable component.

10. The system of claim 1, wherein the at least one adjustable component is configured to be placed percutaneously and expanded across a tricuspid valve of the heart to affect a flow of blood across the at least one adjustable component.

11. The system of claim 1, wherein the at least one adjustable component is configured to be placed percutaneously and expanded in a vena cava within the patient's body with a mechanism to induce a pressure gradient to the flow of blood across the at least one adjustable component.

12. The system of claim 1, wherein the adjustable component comprises a tubular body sized to extend across a tricuspid valve of the heart, the tubular body comprising a lumen communicating between opposite ends of the tubular body, and wherein an open area of the lumen is adjustable to increase or decrease retrograde blood flow across the tricuspid valve.

13. The system of claim 1, wherein the adjustable component comprises an expandable structure including a plurality of splines sized to extend across a tricuspid valve of the patient's heart, the expandable structure being adjustable by at least partially expanding or collapsing intermediate regions of the splines to limit closure of the tricuspid valve to increase or decrease retrograde blood flow across the tricuspid valve.

14. A system configured to be implanted in a patient's body to monitor and/or treat the patient, the system comprising:
   at least one sensor configured to provide sensor data that corresponds to blood flow or blood volume within the patient's heart;
   at least one adjustable component designed to cause regurgitation where blood flows in a direction opposite the normal direction within a region of the patient's heart; and
   a controller configured for adjusting the function of the at least one adjustable component based at least in part on sensor data from the at least one sensor.

15. The system of claim 14, further comprising a pacing component coupled to the controller capable of at least one of sensing and pacing a chamber of the heart.

16. The system of claim 15, wherein the controller is configured to adjust both the pacing component and the adjustable component in response to the sensor data from the at least one sensor.

17. The system of claim 14, further comprising an ac y sensor coupled to the controller configured to identify patient activity coupled to the controller.

18. The system of claim 17, wherein the activity sensor comprises one of an accelerometer or a sensor sensitive to minute ventilation.

19. The system of claim 14, wherein the at least one sensor comprises one of a blood oxygen sensor and a plurality of electrodes configured to measure changes in electrical impedance that correlate with changes in blood volume.

20. The system of claim 14, wherein the at least one adjustable component is configured to be placed percutaneously and expanded across the tricuspid valve to affect the flow of blood across the at least one adjustable component.

* * * * *